United States Patent
Lin et al.

(10) Patent No.: US 12,343,366 B2
(45) Date of Patent: Jul. 1, 2025

(54) PREBIOTIC COMPOSITION AND METHOD FOR IMPROVING INTESTINAL HEALTH USING THE SAME

(71) Applicant: TCI CO., LTD., Taipei (TW)

(72) Inventors: Yung-Hsiang Lin, Taipei (TW); Chu-Han Huang, Taipei (TW)

(73) Assignee: TCI CO., LTD., Taipei (TW)

( * ) Notice: Subject to any disclaimer, the term of this patent is extended or adjusted under 35 U.S.C. 154(b) by 5 days.

(21) Appl. No.: 17/519,595

(22) Filed: Nov. 5, 2021

(65) Prior Publication Data
US 2023/0144246 A1 May 11, 2023

(51) Int. Cl.
| | | |
|---|---|---|
| A61K 31/733 | (2006.01) | |
| A61K 31/702 | (2006.01) | |
| A61K 31/718 | (2006.01) | |
| A61K 36/185 | (2006.01) | |
| A61P 1/14 | (2006.01) | |
| A61P 3/04 | (2006.01) | |

(52) U.S. Cl.
CPC .......... *A61K 36/185* (2013.01); *A61K 31/702* (2013.01); *A61K 31/718* (2013.01); *A61P 1/14* (2018.01); *A61P 3/04* (2018.01)

(58) Field of Classification Search
CPC .. A61K 36/185; A61K 31/702; A61K 31/718; A61P 1/14; A61P 3/04
See application file for complete search history.

(56) References Cited

U.S. PATENT DOCUMENTS 10,512,663 B2 * 12/2019 Ansell ............... A61P 29/00

FOREIGN PATENT DOCUMENTS

| CN | 110934290 | * | 3/2020 | |
| CN | 110934290 A | | 3/2020 | |
| CN | 112708590 A | | 4/2021 | |
| EP | 1243273 A1 | * | 9/2002 | ............ A23K 10/18 |
| JP | 2006089407 A | * | 4/2006 | |
| JP | 2018150262 A | | 9/2018 | |
| KR | 102315134 B1 | * | 10/2021 | |

OTHER PUBLICATIONS

Yang, Hsin-Yi, et al. "Beneficial Effects of Golden Kiwifruit Consumption in Overweight and Obese Young Adults." Journal of nutritional science and vitaminology 66.Supplement (2020): S356-S360 (Year: 2020).*

Nešić, Andrijana, et al. "The kiwifruit allergen act d 1 activates NF-kB signaling and affects mRNA expression of TJ proteins and innate pro-allergenic cytokines." Biomolecules 9.12 (2019): 816 (Year: 2019).*

(Continued)

*Primary Examiner* — Louise W Humphrey
*Assistant Examiner* — Mary A Crum
(74) *Attorney, Agent, or Firm* — Chich-Mei Wang

(57) ABSTRACT

Provided is a prebiotic composition, including a kiwifruit fermented product, inulin, and fructooligosaccharide, where the weight ratio of the kiwifruit fermented product, the inulin, and the fructooligosaccharide is 3-4:2.5-4:2.5-4. A method for improving intestinal health of a subject in need thereof by using the prebiotic composition is also provided.

9 Claims, 8 Drawing Sheets

(56) References Cited

OTHER PUBLICATIONS

Yang, Hsin-Yi, et al. "Beneficial Effects of Golden Kiwifruit Consumption in Overweight and Obese Young Adults." Journal of nutritional science and vitaminology 66.Supplement (2020): S356-S360 (Year: 2020) (Year: 2020).*

Nešić, Andrijana, et al. "The kiwifruit allergen act d 1 activates NF-kB signaling and affects mRNA expression of TJ proteins and innate pro-allergenic cytokines." Biomolecules 9.12 (2019): 816 (Year: 2019) (Year: 2019).*

Antonio Gomez, FOS vs inulin, everything you need to know, published online May 11, 2020 (Year: 2020).*

Burokas, Aurelijus, et al. "Targeting the microbiota-gut-brain axis: prebiotics have anxiolytic and antidepressant-like effects and reverse the impact of chronic stress in mice." Biological psychiatry 82.7 (2017): 472-487 (Year: 2017).*

Parhi, Priyanka, et al. "Effect of inulin and fructooligosaccharide supplementation on the growth and survival of Lactobacillus casei in model sugar systems." Journal of Food Processing and Preservation 45.3 (2021): e15228, published Jan. 2, 2021 (Year: 2021).*

Li, Xingchen, et al. "Effects of six commercial *Saccharomyces cerevisiae* strains on phenolic attributes, antioxidant activity, and aroma of kiwifruit (*Actinidia deliciosa* cv.) wine." BioMed Research International 2017.1 (2017): 2934743. (Year: 2017).*

Examination report dated Jul. 11, 2022, listed in correspondent Taiwan patent application No. 110141425.

TCI's Choice of Golden Formula, Allowing Good Bacteria to Grow in the Intestinal Tract-Golden Formula, Another Choice of High-Quality Prebiotics, Newnutrition, https://www.xinyingyang.com/content-29-24712-1.html, Jul. 31, 2021 Full text.

Examination report dated Jan. 16, 2024, listed in correspondent China patent application No. 202111303863.2 (publication No. CN 116076711 A).

Examination report dated Sep. 24, 2024, listed in correspondent China patent application No. 202111303863.2. (publication No. CN 116076711 A).

Yuan Min-Ian et al., "The Protective Effect of Kiwifruit Polyphenols Extract on Intestinaldamage Caused by High Fat Diet and the Mechanism Involved", School of Pubic Health, Key Laboratory of Environmental Pollution Monitoring and Disease Control, Ministry of Education, Guizhou Medical University, College of Food Science, Guiyang 550025, China, Acata Nutrimenta Sinica, Aug. 2020, vol. 42 No. 4. The 2nd Paragraph of the left column of p. 383, chapter 2.2.1.3.

\* cited by examiner

PREBIOTIC COMPOSITION AND METHOD FOR IMPROVING INTESTINAL HEALTH USING THE SAME

BACKGROUND

Technical Field

The present invention relates to use of a prebiotic composition, and specifically, to use of a kiwifruit fermented product and sugars for preparing the prebiotic composition and use of the prebiotic composition for improving an intestinal tract of a subject.

RELATED ART

Prebiotics are polysaccharides in natural food that are not easily digested by human enzymes, but prebiotics can be utilized by probiotics in the digestive system (mainly the large intestine) in the growth, expansion, and metabolism of bacterial flora, and the production of short chain fatty acids (SFCAs).

Prebiotics are defined as "a substrate that is selectively utilized by host microorganisms conferring a health benefit" according to the joint statement on prebiotics issued by the International Scientific Association for Probiotics and Prebiotics (ISAPP) in the 2017 "Nature report."

Specifically, prebiotics can help the growth of probiotics and help the inhibition of harmful bacteria in the intestinal tract. Probiotics in the intestinal tract can also metabolize prebiotics to produce SFCAs, and then the SFCAs are provided to the probiotics and host as an energy source.

SUMMARY

In view of this, the present invention provides a prebiotic composition, including a kiwifruit fermented product and sugars, and used for improving an intestinal tract of a subject and further assisting the subject in weight loss.

In some embodiments, a prebiotic composition includes a kiwifruit fermented product, inulin, and fructooligosaccharide, where a weight ratio of the kiwifruit fermented product, the inulin, and the fructooligosaccharide is 3-4:2.5-4:2.5-4.

In some embodiments, use of a kiwifruit fermented product and sugars for preparing a prebiotic composition for improving an intestinal tract of a subject is provided, where the prebiotic composition includes a kiwifruit fermented product, inulin, and fructooligosaccharide, and the weight ratio of the kiwifruit fermented product, the inulin, and the fructooligosaccharide is 3-4:2.5-4:2.5-4.

In some embodiments, a method for improving an intestinal tract of a subject in need thereof is provided, including administering an effective dose of a prebiotic composition to the subject. The prebiotic composition includes a kiwifruit fermented product, inulin, and fructooligosaccharide, and a weight ratio of the kiwifruit fermented product, the inulin, and the fructooligosaccharide is 3-4:2.5-4:2.5-4.

In some embodiments, the weight ratio of the kiwifruit fermented product, the inulin, and the fructooligosaccharide that are included in the prebiotic composition is 4:3:3.

In some embodiments, the improvement of the intestinal tract of the subject includes improving intestinal flora, improving bowel movement of the subject, improving intestinal barrier of the subject, or a combination thereof.

In some embodiments, the intestinal flora includes *Akkermansia muciniphila, Parabacteroides goldsteinii*, and *Bifidobacterium*.

In some embodiments, the prebiotic composition is used for promoting the growth of *Parabacteroides goldsteinii*.

In some embodiments, the improvement of the bowel movement of the subject includes reducing defecation difficulty of the subject, promoting intestinal peristalsis frequency of the subject, reducing incomplete defecation of the subject, reducing the defecation time of the subject, or a combination thereof.

In some embodiments, the prebiotic composition is used for increasing a concentration of a tight junction protein in the blood of the subject.

In some embodiments, the tight junction protein is claudin 3 (CLDN3).

In some embodiments, the prebiotic composition is used for reducing the subject's weight, waist circumference, body fat percentage, or a combination thereof.

In some embodiments, the effective dose of the prebiotic composition is 800 mg/day.

In summary, the prebiotic composition of any embodiment includes the kiwifruit fermented product, inulin, and fructooligosaccharide. That is, the kiwifruit fermented product and polysaccharide can be used for preparing the prebiotic composition for improving an intestinal tract of a subject. In some embodiments, the prebiotic composition can be used for improving the intestinal flora, improving bowel movement of the subject, improving the intestinal barrier of the subject, or a combination thereof. For example, the prebiotic composition can promote the growth of probiotics such as *Akkermansia muciniphila, Parabacteroides goldsteinii*, and *Bifidobacterium* and increase the content of the probiotics in the intestinal tract of the subject. In some embodiments, the prebiotic composition can be used for reducing the defecation difficulty of the subject, promoting the intestinal peristalsis frequency of the subject, reducing the incomplete defecation of the subject, reducing the defecation time of the subject, or a combination thereof. In some embodiments, the prebiotic composition can be used for increasing the concentration of tight junction protein (such as CLDN3) in the blood of the subject. In some embodiments, the prebiotic composition is used for reducing the subject's weight, waist circumference, body fat percentage, or a combination thereof, so as to achieve slimming.

DETAILED DESCRIPTION

Figure 1:
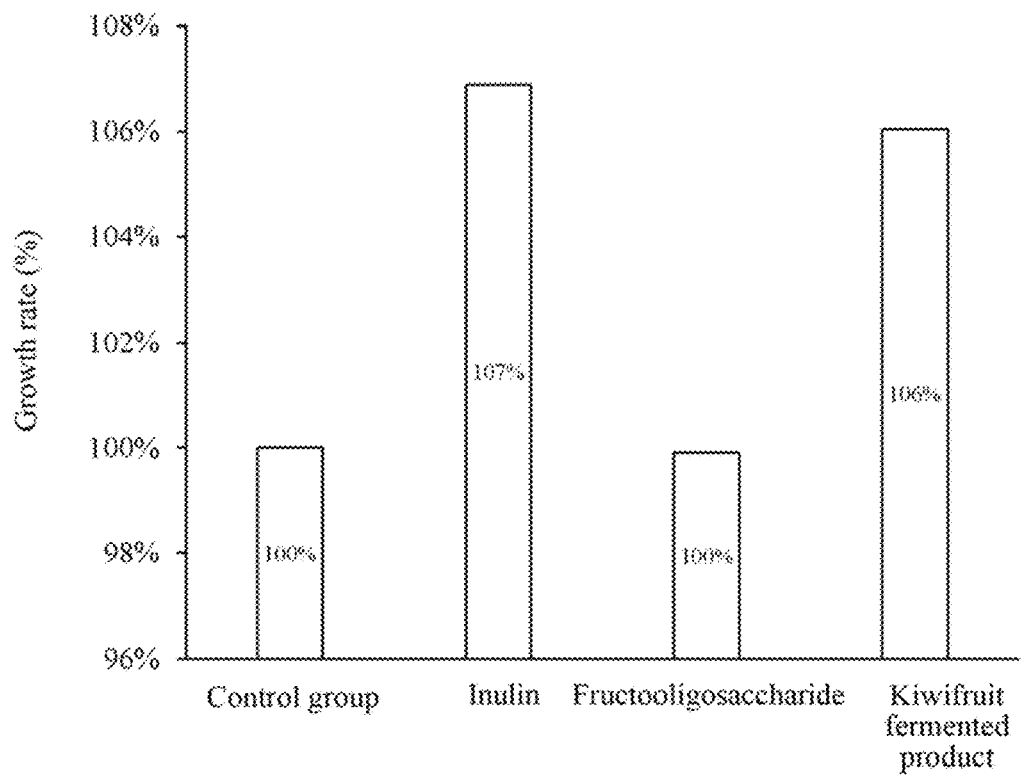
FIG. 1 is a graph showing experimental analysis results of an effect of a single ingredient on probiotic growth.

In the description of the following embodiments, unless otherwise specified, the symbol "%" refers to weight percentage and the symbol "vol %" usually refers to volume percentage.

A prebiotic composition includes a kiwifruit fermented product and sugars. The sugars are polysaccharides such as oligosaccharides and dietary fibers, including fructooligosaccharide and inulin. The kiwifruit fermented product is prepared by fermenting the juice of kiwifruit (*Actinidia deliciosa*) with various bacterial strains.

In some embodiments, the prebiotic composition includes a kiwifruit fermented product, inulin, and fructooligosaccharide, and the weight ratio of the kiwifruit fermented product, the inulin, and the fructooligosaccharide is 3-4:2.5-4:2.5-4. For example, the prebiotic composition includes the kiwifruit fermented product, the inulin, and the fructooligosaccharide with a weight ratio of 4:3:3.

In some embodiments, the preparation of the kiwifruit fermented product includes mixing glucose, kiwifruit, and water with a weight that is 3-6 folds the total weight of the kiwifruit, to obtain a culture liquid; and then fermenting the culture liquid with multiple strains for 1-4 days to obtain a kiwifruit fermented liquid. Herein, the multiple strains include yeast and lactic acid bacteria. Herein, the kiwifruit may include its pulp/fruit, pulp/fruit containing peel, or pulp/fruit containing seeds.

The yeast used may be commercially available *Saccharomyces cerevisiae*. For example, the yeast used may be *Saccharomyces cerevisiae* with a deposit number BCRC20271 (an international deposit number ATCC26602) purchased from the Food Industry Research and Development Institute.

The lactic acid bacteria used may be commercially available *Lactobacillus helveticus, Streptococcus thermophilus*, or *Lactobacillus plantarum*. For example, the lactic acid bacteria used may be *Lactobacillus helveticus* TC1357 (with a deposit number BCRC910846 from the Food Industry Research and Development Institute and an international deposit number DSM33107), *Streptococcus thermophilus* TC1028 with a deposit number BCRC910805 (an international deposit number DSM33108), *Streptococcus thermophilus* TC1378 with a deposit number BCRT910760 (an international deposit number DSM32451), or *Streptococcus thermophilus* TC1633 with a deposit number BCRC910636 (an international deposit number DSM28121).

For example, first, the kiwifruit and water are mixed and then subjected to extraction at 80-100° C. for 0.5-1.5 h to obtain a kiwifruit extract; then, glucose is added into the kiwifruit extract to obtain a culture liquid for subsequent fermentation. The addition amount of the glucose is 8-10% of the total weight of the kiwifruit and water. In addition, the culture liquid has adequate sugar due to the addition of glucose, so that the strains have adequate nutrients for subsequent fermentation. Next, the yeast is first added into the culture liquid to ferment for 0.5-2 days to form an initial fermentation broth, the lactic acid bacteria are then added into the initial fermentation broth to ferment for 0.5-2 days to form a kiwifruit fermented liquid, and the kiwifruit fermented liquid is filtered, concentrated, freeze-dried, and crushed to obtain a kiwifruit fermented product. In some embodiments, the total polyphenol content of the kiwifruit fermented liquid is 200-220 μg/mL.

Based on this, the kiwifruit fermented product obtained by the foregoing specific process is mixed with inulin and fructooligosaccharide in a specific ratio to obtain a prebiotic composition. The weight ratio of the kiwifruit fermented product, the inulin, and the fructooligosaccharide is 34:2.54:2.54. The prebiotic composition can increase the quantity of probiotics in the intestinal tract of a subject by at least 3 folds.

In some embodiments, the prebiotic composition can improve the bacterial flora of the intestinal tract. For example, the prebiotic composition can increase the quantity of *Akkermansia muciniphila* in the intestinal tract of a subject by at least 3 folds, the prebiotic composition can increase the quantity of *Parabacteroides goldsteinii* in the intestinal tract of a subject by at least 1.5 folds, and the prebiotic composition can increase the quantity of *Bifidobacterium* in the intestinal tract of a subject by at least 3 folds.

In some embodiments, the prebiotic composition can improve bowel movement of a subject. For example, the administration of the prebiotic composition can reduce the defecation frequency and defecation time of a subject to reduce the defecation difficulty of the subject, reduce the frequency of the incomplete defecation of the subject, and promote the intestinal peristalsis frequency, thereby improving bowel movement of the subject.

In some embodiments, the prebiotic composition can increase the concentration of tight junction protein in the blood of a subject, thereby improving the intestinal barrier of the subject. For example, the tight junction protein may be CLDN3.

Therefore, the prebiotic composition can improve the intestinal tract of a subject. Herein, the subject is a human.

In some embodiments, the prebiotic composition can improve the intestinal tract of a subject, thereby achieving weight loss. For example, the administration of the prebiotic composition can reduce the subject's weight, waist circumference, body fat percentage, or a combination thereof. The body fat percentage includes a whole body fat percentage and a trunk fat percentage.

In some embodiments, the prebiotic composition may be solid, such as powder, tablets, or capsules.

In some embodiments, the dose of the prebiotic composition is 800 mg/day. For example, the prebiotic composition is mainly composed of a kiwifruit fermented product, inulin, and fructooligosaccharide, and the dose 800 mg/day of the prebiotic composition refers to that the total amount of the kiwifruit fermented product, the inulin, and the fructooligosaccharide is 800 mg.

Any prebiotic composition above may be a medicament. In other words, the medicament contains an effective content of kiwifruit fermented product, inulin, and fructooligosaccharide in a specific ratio.

In some embodiments, the foregoing medicament may be manufactured into a dosage form suitable for enteral, parenteral, oral, or topical administration using techniques well known to those skilled in the art.

In some embodiments, the dosage form for enteral or oral administration includes, but is not limited to: a tablet, a troche, a lozenge, a pill, a capsule, a dispersible powder or granule, a solution, a suspension, an emulsion, a syrup, an elixir, a slurry, or other similar substances. In some embodiments, the dosage form for parenteral or topical administration includes, but is not limited to: an injection, a sterile powder, an external preparation, or other similar substances. In some embodiments, the administration manner of the injection may be subcutaneous injection, intraepidermal injection, intradermal injection, or intralesional injection.

In some embodiments, the foregoing medicament may include a pharmaceutically acceptable carrier widely used in drug manufacturing technology. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, or other similar substances. The type and quantity of selected carriers fall within the scope of professionalism and routine technology of those skilled in the art. In some embodiments, the solvent of the pharmaceutically acceptable carrier may be water, normal saline, phosphate buffered saline (PBS), or aqueous solution containing alcohol.

In some embodiments, any prebiotic composition above may be an edible product. In other words, the edible product contains a specific content of kiwifruit fermented product, inulin, and fructooligosaccharide in a specific ratio. In some embodiments, the edible product may be a general food, a food for special health use (FoSHU), or a dietary supplement.

In some embodiments, the foregoing edible product may be manufactured into a dosage form suitable for oral administration using techniques well known to those skilled in the art. In some embodiments, the foregoing general food may be the edible product itself. In some embodiments, the general food may be, but is not limited to: beverages, fermented foods, bakery products, or condiments.

In some embodiments, the obtained prebiotic composition may also be a food additive to prepare a food composition containing the prebiotic composition prepared from the kiwifruit fermented product, inulin, and fructooligosaccharide in a specific ratio. Herein, the prebiotic composition of any embodiment can be added during the preparation of raw materials by conventional methods, or the prebiotic composition of any embodiment can be added during food making, to prepare an edible product (that is, a food composition) for humans and non-human animals with any edible material.

Example 1: Preparation of Kiwifruit Fermented Product

First, kiwifruits (*Actinidia deliciosa*) were thoroughly washed and crushed into kiwifruit pieces with a size of less than 12 mm. The kiwifruit pieces and water were uniformly mixed in a ratio of 1:5 to obtain a raw material mixed liquid. Then, glucose of 7.5% of the total weight of the raw material mixed liquid was added into the raw material mixed liquid, and then the raw material mixed liquid was subjected to extraction at 95° C. for 0.5 h, to obtain a kiwifruit culture liquid. Herein, the degree Brix of the culture liquid was 8.0° Bx.

The culture liquid was cooled to room temperature for fermentation. *Saccharomyces cerevisiae* (purchased from Bioresource Collection and Research Center (BCRC) of Food Industry Research and Development Institute with a deposit number of BCRC20271) of 0.1% of the kiwifruit culture liquid was first added into the kiwifruit culture liquid to ferment at 30° C. for 1 day to form an initial fermentation broth, and *Streptococcus thermophilus* (purchased from BCRC with a deposit number of BCRC910636) of 0.05% of the kiwifruit culture liquid was then added into the initial fermentation broth to ferment at 30° C. for 1 day to obtain a kiwifruit fermented liquid. Herein, the default specification of the kiwifruit fermented liquid included the pH value of 3.5+0.3 and the degree Brix of less than 4.0° Bx. It can be determined that the fermentation is completed if the kiwifruit fermented liquid meets the default specification. In this case, most of sugars in the kiwifruit fermented liquid had been exhausted.

Then, the kiwifruit fermented liquid was filtered with a 200-mesh filter to remove the fruit residue from the fermented liquid, and then freeze-dried and crushed to obtain a kiwifruit fermented product.

Example 2: Effect of Single Ingredient on Probiotic Growth

Herein, the single ingredient refers to the kiwifruit fermented product prepared in Example 1, fructooligosaccharide (purchased from Meiji), and inulin (purchased from Cosucra). The probiotic refers to *Parabacteroides goldsteinii* (purchased from ATCC). The liquid culture medium used is a tryptone soy broth (TSB, hereinafter referred to as a TSB culture medium) with 5% of sheep blood (purchased from BD).

There were one control group and three experimental groups. The control group adopted the liquid culture medium (that is, 95% of TSB culture medium with 5% of sheep blood). The three experimental groups were respectively a kiwifruit fermented product group, an inulin group, and a fructooligosaccharide group. The culture medium used by the kiwifruit fermented product group included 94% of TSB culture medium, 5% of sheep blood, and 1% of the kiwifruit fermented product prepared in Example 1. The culture medium used by the inulin group included 94% of TSB culture medium, 5% of sheep blood, and 1% of inulin. The culture medium used by the fructooligosaccharide group included 94% of TSB culture medium, 5% of sheep blood, and 1% of fructooligosaccharide.

1% of activated *Parabacteroides goldsteinii* was added into a 15 mL test tube containing 5 mL of culture medium in each group, and then cultured anaerobically at 37° C. for 48 h. Then, after 48 hours of culture, 100 µL of bacterial liquid in each group was added to a solid TSB culture medium with 5% of sheep blood, and a colony-forming unit (CFU) of each group was calculated. Herein, the growth rate of the CFU of the control group was regarded as 100% to correspondingly calculate growth rates (%) of other groups.

Referring to FIG. 1, the growth rate of the control group without the single ingredient to be tested was 100%, the growth rate of the kiwifruit fermented product group was 106%, the growth rate of the inulin group was 107%, and the growth rate of the fructooligosaccharide group was 100%. Based on this, 1% of fructooligosaccharide did not promote the growth of *Parabacteroides goldsteinii*, but 1% of inulin and 1% of kiwifruit fermented product both increased its colony quantity and promoted its growth.

Example 3: Effect of Different Ingredients on Probiotic Growth

Herein, the prebiotics used include inulin (purchased from Cosucra), xylooligosaccharide (purchased from Shandong Longlive Bio-Technology Co., Ltd.), fnuctooligosaccharide (purchased from Meiji), pomegranate enzyme, and the kiwifruit fermented product prepared in Example 1. The liquid culture medium used is a tryptone soy broth (TSB, hereinafter referred to as a TSB culture medium) with 5% of sheep blood (purchased from BD).

The preparation of the pomegranate enzyme was that: pomegranates (*Punica granatum*) were thoroughly washed and crushed into pomegranate pieces with a size of less than 12 mm. The pomegranate pieces and water were uniformly mixed in a ratio of 1:5 to obtain a raw material mixed liquid. Then, glucose of 7.5% of the total weight of the raw material mixed liquid was added into the raw material mixed liquid, and then the raw material mixed liquid was subjected to extraction at 95° C. for 0.5 h, to obtain a pomegranate culture liquid. Herein, the degree Brix of the culture liquid was 8.0° Bx. The culture liquid was cooled to room temperature for fermentation. *Saccharomyces cerevisiae* (purchased from Bioresource Collection and Research Center (BCRC) of Food Industry Research and Development Institute with a deposit number of BCRC20271) of 0.1% of the pomegranate culture liquid was first added into the pomegranate culture liquid to ferment at 30° C. for 1 day to form an initial fermentation broth, and *Streptococcus thermophilus* (purchased from BCRC with a deposit number of BCRC910636) of 0.05% of the pomegranate culture liquid was then added into the initial fermentation broth to ferment at 30° C. for 1 day to obtain a pomegranate fermented liquid. Herein, the default specification of the pomegranate fermented liquid included the pH value of 3.5±0.3 and the degree Brix of less than 4.0° Bx. It can be determined that the fermentation is completed if the kiwifruit fermented liquid meets the default specification. In this case, most of sugars in the pomegranate fermented liquid had been exhausted. Then, the pomegranate fermented liquid was filtered with a 200-mesh filter to remove the fruit residue from the fermented liquid, and then freeze-dried and crushed to obtain a pomegranate enzyme.

There were one blank group, one experimental group, and seven control groups (groups A-G). The culture medium composition of each of the groups is shown in Table 1.

TABLE 1

| Group | Culture medium composition | Composition of prebiotic combination in each group |
|---|---|---|
| Blank group | 95% TSB culture medium + 5% sheep blood | None |
| Experimental group | 94% TSB culture medium + 5% sheep blood + 1% experimental group prebiotic combination (i.e., prebiotic composition) | 40% kiwifruit fermented product + 30% inulin + 30% fructooligosaccharide |
| Control group A | 94% TSB culture medium + 5% sheep blood + 1% prebiotic combination A | 40% pomegranate enzyme + 30% inulin + 30% xylooligosaccharide |
| Control group B | 94% TSB culture medium + 5% sheep blood + 1% prebiotic combination B | 40% pomegranate enzyme + 30% fructooligosaccharide + 30% xylooligosaccharide |
| Control group C | 94% TSB culture medium + 5% sheep blood + 1% prebiotic combination C | 40% pomegranate enzyme + 30% inulin + 30% fructooligosaccharide |
| Control group D | 94% TSB culture medium + 5% sheep blood + 1% prebiotic combination D | 25% pomegranate enzyme + 25% inulin + 25% xylooligosaccharide + 25% fructooligosaccharide |
| Control group E | 94% TSB culture medium + 5% sheep blood + 1% prebiotic combination E | 40% kiwifruit fermented product + 30% inulin + 30% xylooligosaccharide |
| Control group F | 94% TSB culture medium + 5% sheep blood + 1% prebiotic combination F | 40% kiwifruit fermented product + 30% fructooligosaccharide + 30% xylooligosaccharide |
| Control group G | 94% TSB culture medium + 5% sheep blood + 1% prebiotic combination G | 25% kiwifruit fermented product + 25% inulin + 25% xylooligosaccharide + 25% fructoolingosaccharide |

It can be learned from the table that the experimental group and control groups (groups A-G) used the culture medium of 94% TSB culture medium+5% sheep blood+1% prebiotic combination (the experimental group prebiotic combination (i.e., prebiotic composition) and the prebiotic combinations groups A-G) except that the blank group used the liquid culture medium (that is, 95% of TSB culture medium with 5% of sheep blood). The culture medium of the experimental group is used as an example. 100 mL of the culture medium included 99 mL of liquid culture medium (including 94 mL of TSB culture medium and 5% of sheep blood) and 1 mL of the experimental group prebiotic combination. 1 mL of the experimental group prebiotic combination was composed of 400 μL of 10% kiwifruit fermented product, 300 μL of 10% fructooligosaccharide solution, and 300 μL of 10% inulin solution. The culture medium of other groups had similar composition.

1% of activated *Parabacteroides goldsteinii* was added into a 15 mL test tube containing 5 mL of culture medium in each group, and then cultured anaerobically at 37° C. for 48 h. Then, after 48 hours of culture, 100 μL of bacterial liquid in each group was added to a solid TSB culture medium with 5% of sheep blood, and a colony-forming unit (CFU) of each group was calculated. Herein, the growth rate of the CFU of the control group was regarded as 100% to correspondingly calculate growth rates (%) of other groups.

Figure 2:
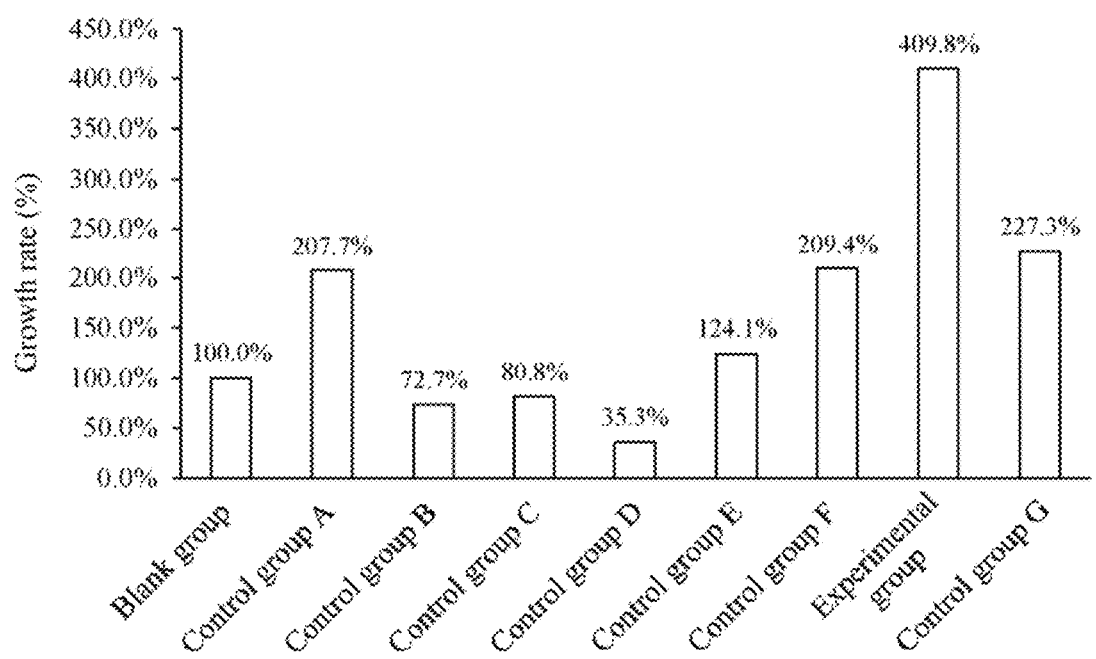
FIG. 2 is a graph showing experimental analysis results of effects of multiple groups with different ingredients on probiotic growth.

Referring to FIG. 2, the growth rate of the blank group without prebiotic combination was 100%, the growth rate of the experimental group was 409.8% (almost 4.1 folds), the growth rate of the control group A was 207.7%, the growth rate of the control group B was 72.7%, the growth rate of the control group C was 80.8%, the growth rate of the control group D was 35.3%, the growth rate of the control group E was 124.1%, the growth rate of the control group F was 209.4%, and the growth rate of the control group G was 227.3%. Based on this, the prebiotic composition composed of 40% kiwifruit fermented product, 30% inulin, and 30% fructooligosaccharide significantly improved the growth of *Parabacteroides goldsteinii* and increased the colony quantity thereof.

Based on this, a specific prebiotic combination can effectively and significantly improve the growth of probiotics (such as *Parabacteroides goldsteinii*), and not all combinations of common prebiotics (such as inulin, fructooligosaccharide, and xylooligosaccharide) can effectively improve the growth of any probiotics (such as *Parabacteroides goldsteinii*).

Example 4: Effect of Prebiotic Composition with Different Proportions on Probiotic Growth Herein, the prebiotic composition used includes inulin (purchased from Cosucra), fructooligosaccharide (purchased from Meiji), and the kiwifruit fermented product prepared in Example 1. The probiotic refers to *Parabacteroides goldsteinii* (purchased from ATCC). The liquid culture medium used is a tryptone soy broth (TSB, hereinafter referred to as a TSB culture medium) with 5% of sheep blood (purchased from BD).

There were one control group and four experimental groups (groups a-d). The culture medium composition of each of the groups is shown in Table 2.

TABLE 2

| Group | Culture medium composition | Proportion of prebiotic composition | | |
|---|---|---|---|---|
| | | Kiwifruit fermented product | Fructooligo-saccharide | Inulin |
| Experimental group a | 94% TSB culture medium + 5% sheep blood + 1% prebiotic composition a | 30% | 30% | 40% |
| Experimental group b | 94% TSB culture medium + 5% sheep blood + 1% prebiotic composition b | 30% | 40% | 30% |
| Experimental group c | 94% TSB culture medium + 5% sheep blood + 1% prebiotic composition c | 40% | 30% | 30% |
| Experimental group d | 94% TSB culture medium + 5% sheep blood + 1% prebiotic composition d | 50% | 25% | 25% |
| Control group | 95% TSB culture medium + 5% sheep blood | None | | |

It can be learned from the table that the weight ratio of kiwifruit fermented product, fructooligosaccharide, and inulin in each group is 3-4:2.5-4:2.5-4.

1% of activated *Parabacteroides goldsteinii* was added into a 15 mL test tube containing 5 mL of culture medium in each group, and then cultured anaerobically at 37° C. for 48 h. Then, after 48 hours of culture, 100 μL of bacterial liquid in each group was added to a solid TSB culture medium with 5% of sheep blood, and a colony-forming unit (CFU) of each group was calculated. Herein, the growth rate of the CFU of the control group was regarded as 100% to correspondingly calculate growth rates (%) of other groups.

Figure 3:
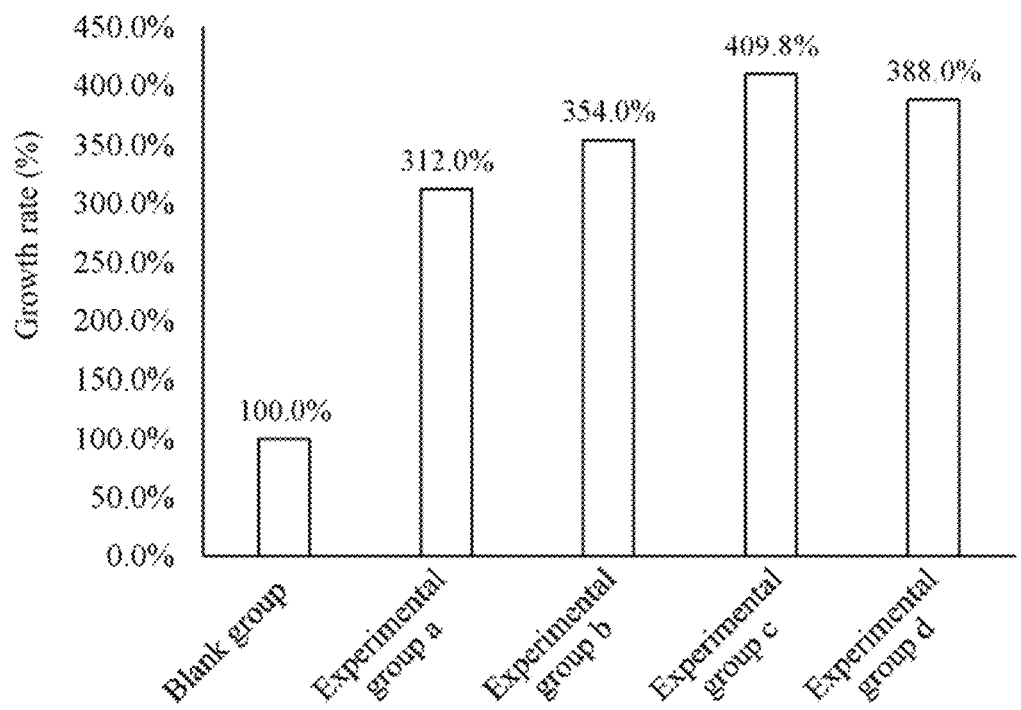
FIG. 3 is a graph showing experimental analysis results of effects of multiple groups of prebiotic composition with different proportions on probiotic growth.

Referring to FIG. 3, the growth rate of the control group without prebiotic composition was 100%, the growth rate of the experimental group a was 312.0% (almost 3.12 folds), the growth rate of the experimental group b was 354.0% (almost 3.54 folds), the growth rate of the experimental group c was 409.8% (almost 4.1 folds), and the growth rate of the experimental group d was 388.0% (almost 3.88 folds). In other words, the prebiotic composition composed of the kiwifruit fermented product, fructooligosaccharide, and inulin effectively improved the growth of *Parabacteroides goldsteinii* by at least 3 folds. In addition, the prebiotic composition with 40% of kiwifruit fermented product, 30% of inulin, and 30% of fructooligosaccharide significantly improved the growth of *Parabacteroides goldsteinii* by at least 4 folds.

Based on this, a specific prebiotic composition with a specific proportion can effectively and significantly improve the growth of probiotics (such as *Parabacteroides goldsteinii*).

Example 5: Human Subject Experiment

To further confirm the effect of a specific prebiotic composition on human body, 8 subjects each took two capsules each containing 400 mg of prebiotic composition composed of the kiwifruit fermented product prepared in Example 1, inulin (purchased from Cosucra), and fructooligosaccharide (purchased from Meiji) in a weight ratio of 4:3:3 per day for 4 weeks. That is, the dose of each subject per day was 800 mg of prebiotic composition. In addition, items such as phlebotomy, stool sampling, questionnaire feedback, and body composition determination were carried out at week 0 (i.e., before taking), week 2 (i.e., after 2 weeks of taking), and week 4 (i.e., after 4 weeks of taking).

The phlebotomy is to determine the content of intestinal barrier protein. The basic structure of the intestinal barrier is formed through co-construction of intestinal epithelial cells by tight junction protein, where the construction is also referred to as tight junction (T). Therefore, the tight junction protein (such as CLDN3 and OCLN) is also referred to as the intestinal barrier protein. The index protein of this blood test was CLDN3. It includes four transmembrane structures that are main composition of the tight junction structure.

The stool sampling is to determine the growth of intestinal bacterial flora. The tested strains were *Akkermansia muciniphila*, *Parabacteroides goldsteinii*, and *Bifidobacterium*.

The questionnaire feedback is defecation questionnaire feedback.

The body composition determination includes weight, body fat percentage, and waist circumference.

Example 5-1. Analysis of CLDN3 Content in Subject's Blood 6 mL of venous blood of each of 8 subjects before taking the prebiotic composition (that is, at week 0) and after taking the prebiotic composition (that is, at week 2 and week 4) was collected by using a purple-top blood collection tube containing EDTA as an anticoagulant, and the analysis of the expression of the intestinal barrier protein content in the blood was carried out by TCI GENE.

Herein, the detected intestinal barrier protein was CLDN3.

Figure 4:
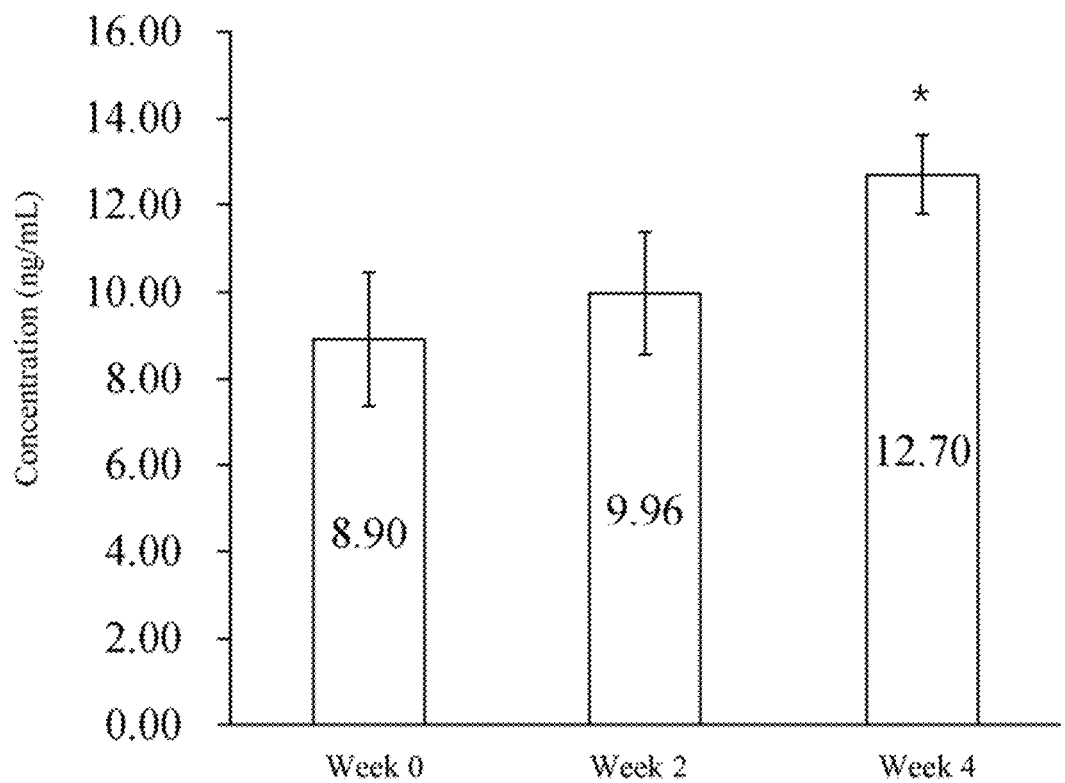
FIG. 4 is a graph showing an experimental result of a prebiotic composition on the expression level of tight junction protein in the blood of a subject.

Referring to FIG. 4, the 8 subjects had an average concentration of CLDN3 in the blood at week 0 of 8.9 ng/mL, had an average concentration of CLDN3 in the blood after 2 weeks of prebiotic composition taking increased to 9.96 ng/mL, and had an average concentration of CLDN3 in the blood after 4 weeks of prebiotic composition taking increased to 12.70 ng/mL. That is, the average concentration of CLDN3 in the blood after 2 weeks of prebiotic composition taking was increased by 1.06 ng/mL, and the average concentration of CLDN3 in the blood after 4 weeks of prebiotic composition taking was increased by 3.8 ng/mL. Based on this, the administration of prebiotic composition effectively increased the concentration of CLDN3, thereby improving the intestinal barrier.

Example 5-2. Analysis on Intestinal Bacterial Flora of Subject

Feces of each of 8 subjects before taking the prebiotic composition (that is, at week 0) and after taking the prebiotic composition (that is, at week 2 and week 4) were collected, and the NGS analysis of feces bacterial flora (at the sequencing position of 16S rRNA V3-V4) was carried out by BIOTOOLS. The analysis results of the 8 subjects were recorded as shown in FIG. 5 to FIG. 7.

Herein, the analyzed strains were *Akkermansia muciniphila* (AKK), *Parabacteroides goldsteinii* (PG), and *Bifidobacterium* (BF).

Figure 5:
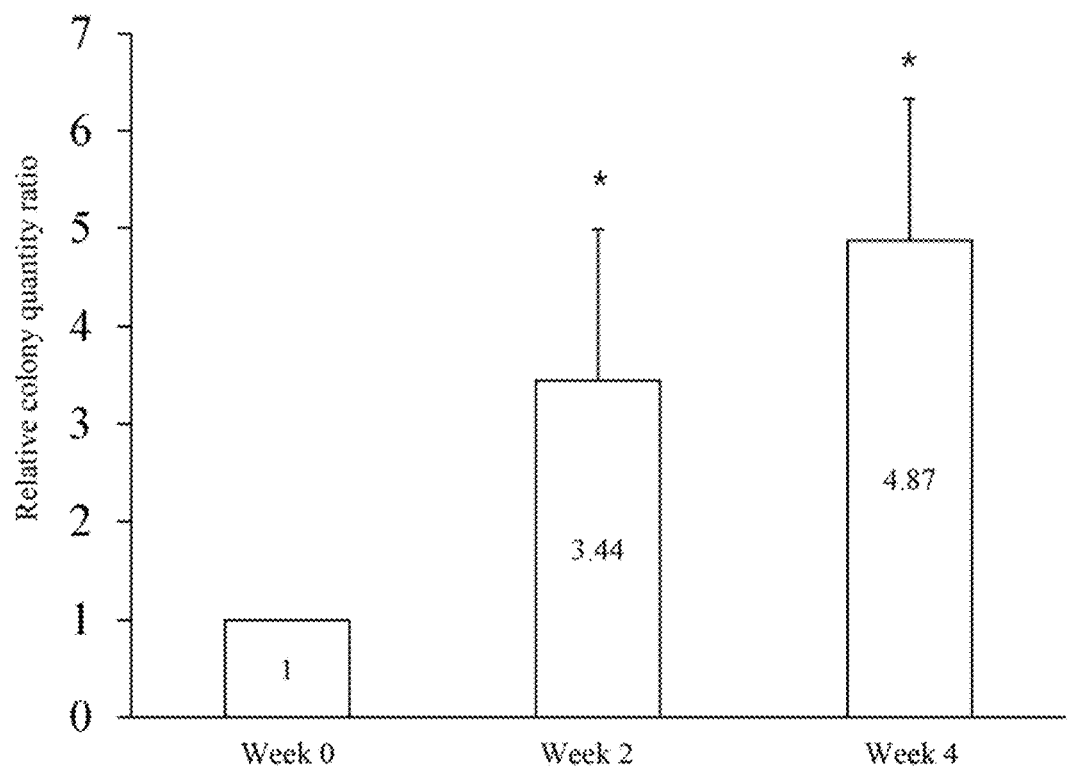
FIG. 5 is a graph showing an experimental result of a prebiotic composition on the growth of *Akkermansia muciniphila;*

Referring to FIG. 5, the average colony quantity ratio of AKK of the 8 subjects at week 2 and week 4 was calculated based on the average colony quantity of AKK of the 8 subjects at week 0 as 1. Based on this, the 8 subjects had an average colony quantity ratio of AKK at week 2 of 3.44, and had an average colony quantity ratio of AKK at week 4 of 4.87. That is, the colony quantity of AKK in the intestinal tract of the 8 subjects was increased by 4.87 folds after 4 weeks of prebiotic composition taking, and the metabolites of AKK suppressed the host's appetite and induced the expression of the host's fasting-induced adipose factor (FIAF) gene, thereby reducing the host's ability to store fat. In addition, the increase of colony quantity of AKK in the intestinal tract can reverse obesity caused by high-fat diet, reduce the concentration of lipopolysaccharide of harmful bacteria in the blood, thereby reducing chronic inflammation and reducing insulin resistance. Therefore, the administration of prebiotic composition composed of kiwifruit fermented product, inulin, and fructooligosaccharide effectively increased the colony quantity of AKK in the intestinal tract of takers, thereby losing weight, reducing chronic inflammation, and reducing insulin resistance.

Figure 6:
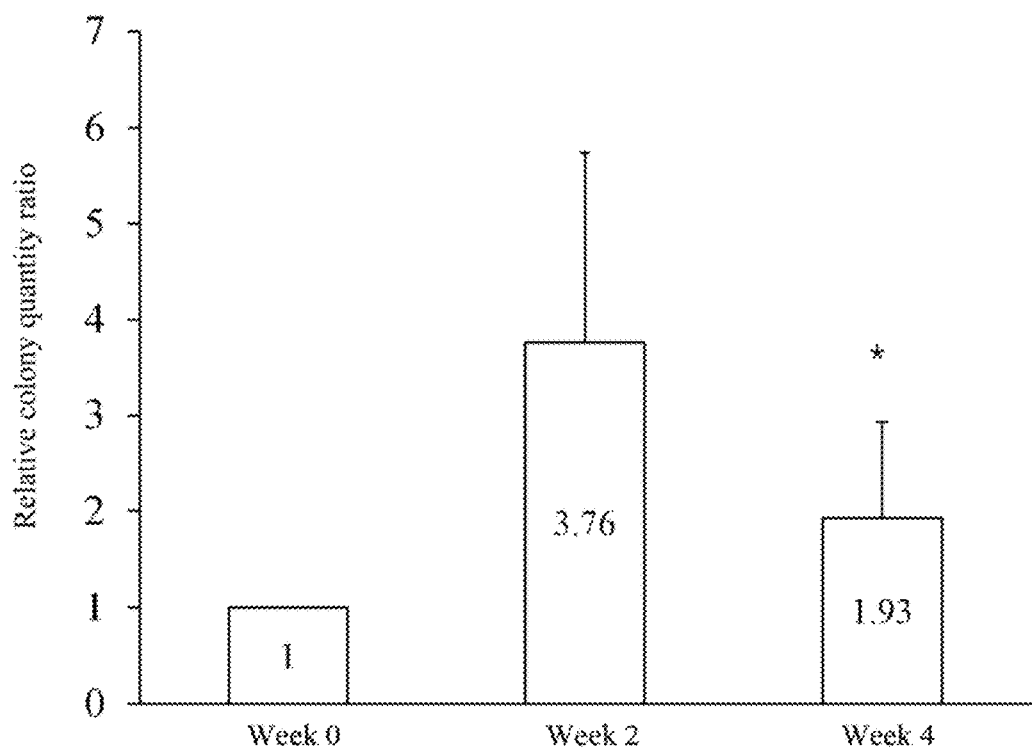
FIG. 6 is a graph showing an experimental result of a prebiotic composition on the growth of *Parabacteroides goldsteinii;*
Figure 7:
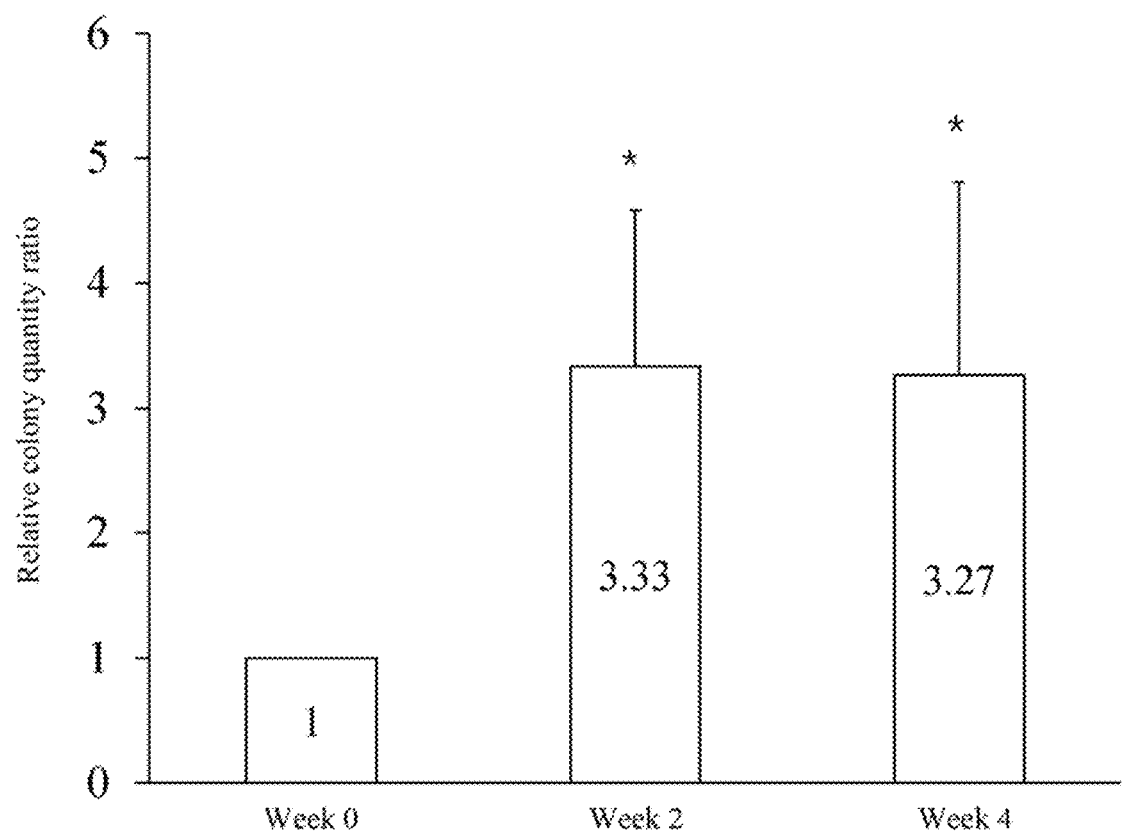
FIG. 7 is a graph showing an experimental result of a prebiotic composition on the growth of *Bifidobacterium;*

Referring to FIG. 6, the average colony quantity ratio of PG of the 8 subjects at week 2 and week 4 was calculated based on the average colony quantity of PG of the 8 subjects at week 0 as 1. Based on this, the 8 subjects had an average colony quantity ratio of PG at week 2 of 3.76, and had an average colony quantity ratio of PG at week 4 of 1.93. That is, the colony quantity of PG in the intestinal tract of the 8 subjects was increased by 1.93 folds after 4 weeks of prebiotic composition taking. In addition, the increase of PG can improve metabolic syndrome, reduce intestinal permeability, and improve intestinal inflammation. Specifically, the increase in colony quantity of PG in the intestinal tract can reduce the host's body weight, slow down the host's insulin resistance, and increase the host's fat metabolism and activate the brown cells in the host, thereby achieving slimming. Therefore, the administration of prebiotic composition composed of kiwifruit fermented product, inulin, and fructooligosaccharide effectively increased the colony quantity of PG in the intestinal tract of takers, thereby losing weight, reducing intestinal permeability, and improving intestinal inflammation.

Referring to FIG. 7, the average colony quantity ratio of BF of the 8 subjects at week 2 and week 4 was calculated based on the average colony quantity of BF of the 8 subjects at week 0 as 1. Based on this, the 8 subjects had an average colony quantity ratio of BF at week 2 of 3.33, and had an average colony quantity ratio of BF at week 4 of 3.27. That is, the colony quantity of BF in the intestinal tract of the 8 subjects was increased by 3.27 folds after 4 weeks of prebiotic composition taking. In addition, BF as physiologically beneficial bacteria has various important physiological functions, such as improving biological barrier, improving nutrition, anti-tumor, immune enhancement, improving gastrointestinal function, and anti-aging, for the host's health. Therefore, the administration of prebiotic composition composed of kiwifruit fermented product, inulin, and fructooligosaccharide effectively increased the colony quantity of BF in the intestinal tract of takers, thereby improving biological barrier, improving nutrient absorption, improving anti-tumor capability, enhancing immunity, and improving gastrointestinal function.

Example 5-3. Analysis on Defecation Questionnaire of the Subjects

Bowel movement of 8 subjects before taking the prebiotic composition (that is, at week 0) and after taking the prebiotic composition (that is, at week 2 and week 4) was investigated with a questionnaire. The questionnaire feedback results of the 8 subjects were recorded as shown in FIG. 8 to FIG. 11.

Herein, as shown in FIG. 3, items in the questionnaire for analysis included: defecation difficulty (such as defecation frequency, defecation time, and defecation completion) and intestinal peristalsis frequency.

TABLE 3

| Comprehensive assessment of bowel movement | | | | |
|---|---|---|---|---|
| Bowel movement/Intestinal condition | Option | | | |
| 1. How often do you defecate? | ☐ Once a day | ☐ Twice a day or more | ☐ Once every two days | |
| 2. How long does it take to defecate in the toilet? | ☐ Less than 5 minutes | ☐ 5-10 minutes | ☐ 10-20 minutes | |
| 3. How often did you feel incomplete defecation in the past period of time? | ☐ No | ☐ Rarely | ☐ Sometimes | ☐ Often |
| 4. How often did you feel intestinal peristalsis in the past period of time? | ☐ No | ☐ Rarely | ☐ Sometimes | ☐ Often |

Figure 8:
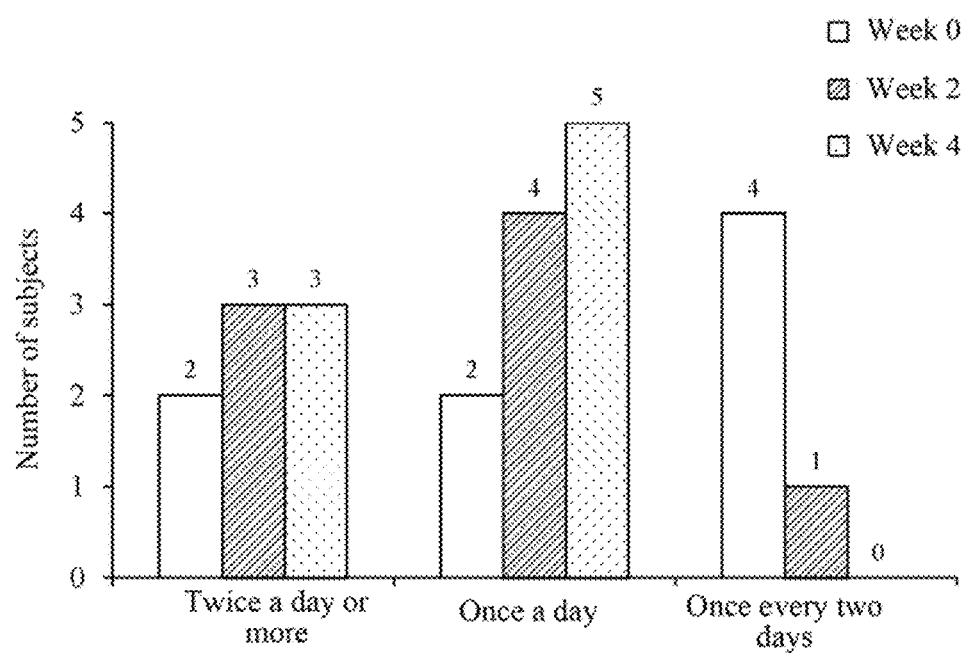
FIG. 8 is a graph showing an analysis result of a prebiotic composition on the average defecation frequency of subjects.

Referring to FIG. 8, before taking the prebiotic composition at week 0, 4 out of 8 subjects (i.e., 50% of the subjects) defecated once every two days or more, but after taking the prebiotic composition for 2 weeks, the quantity of the subjects who defecated once every two days or more was reduced to 1, and there were 4 subjects who defecate once a day and 3 subjects who defecate twice a day or more. However, after taking the prebiotic composition for 4 weeks, all subjects (i.e., 100% of the subjects) defecated every day, where there were 5 subjects who defecate once a day and 3 subjects who defecate twice a day or more. Based on this, the administration of prebiotic composition improved the defecation frequency (at least once a day) of the subjects, thereby facilitating natural cleansing of the colon of the subjects.

Figure 9:
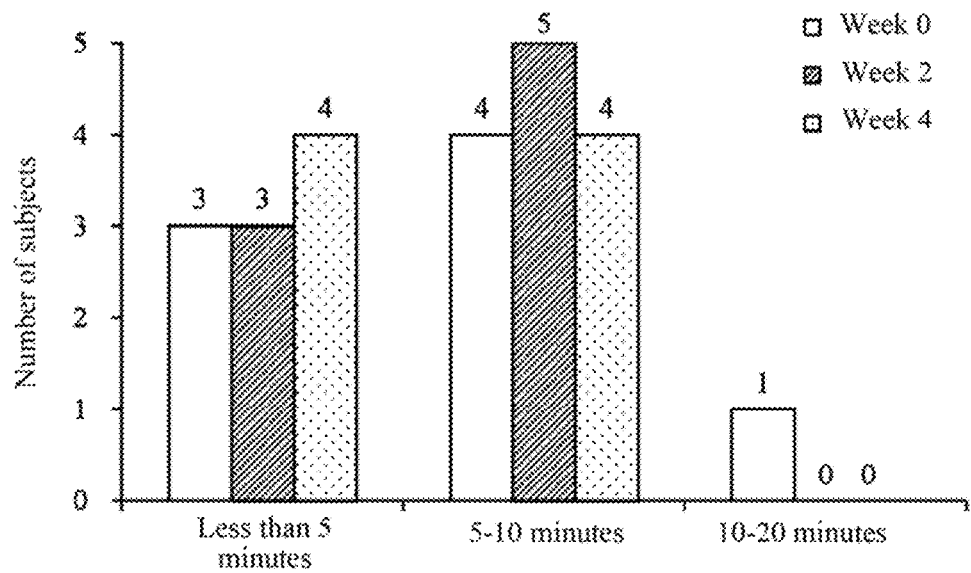
FIG. 9 is a graph showing an analysis result of a prebiotic composition on the average defecation time of subjects.

Referring to FIG. 9, before taking the prebiotic composition at week 0, in the 8 subjects, 1 subject required a defecation time of 10-20 minutes, 4 subjects required a defecation time of 5-10 minutes, and 3 subjects required a defecation time of less than 5 minutes. However, after taking the prebiotic composition for 2 weeks, no subject required a defecation time of more than 10 minutes, where there were 5 subjects requiring a defecation time of 5-10 minutes and 3 subjects requiring a defecation time of less than 5 minutes. Moreover, after taking the prebiotic composition for 4 weeks, similar to the results at week 2, no subject requires a defecation time of more than 10 minutes, where there were 4 subjects requiring a defecation time of 5-10 minutes and 4 subjects requiring a defecation time of less than 5 minutes, that is, 50% of the subjects required a defecation time of less than 5 minutes, and 100% of the subjects required a defecation time of less than 10 minutes. Based on this, the administration of prebiotic composition improved the defecation time of subjects, thereby avoiding problems (such as numb feet and nerve compression) caused by sitting on the toilet for a long time, and reducing the time of using the toilet.

Figure 10:
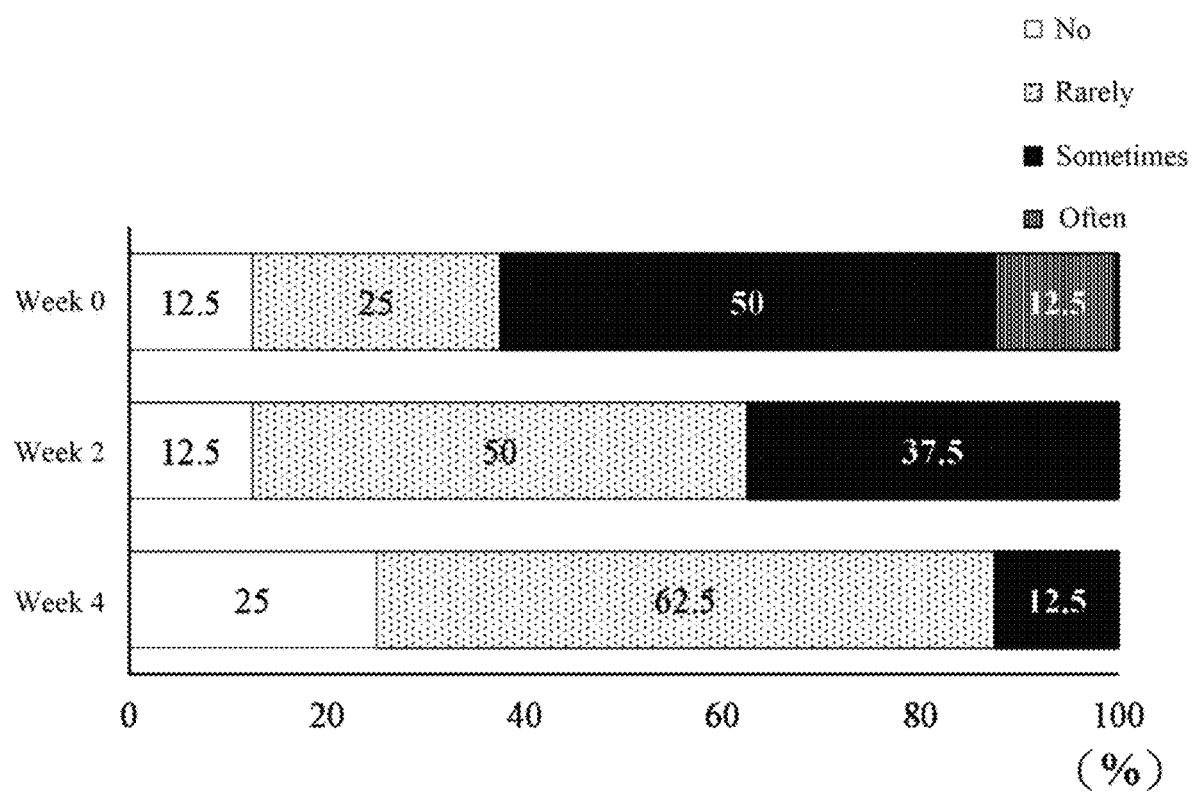
FIG. 10 is a graph showing an analysis result of a prebiotic composition on the frequency of incomplete defecation of subjects.

Referring to FIG. 10, before taking the prebiotic composition at week 0, in the 8 subjects, 50% of the subjects "sometimes" felt incomplete defecation, 12.5% of the subjects "often" felt incomplete defecation, 25% of the subjects "rarely" felt incomplete defecation, and 12.5% of the subjects felt "no" incomplete defecation. After taking the prebiotic composition for 2 weeks, 50% of the subjects "rarely" felt incomplete defecation, 12.5% of the subjects felt "no" incomplete defecation, and no subject "often" felt incomplete defecation. Only 37.5% of the subjects "sometimes" felt incomplete defecation. After taking the prebiotic composition for 4 weeks, 62.5% of the subjects "rarely" felt incomplete defecation, 25% of the subjects felt "no" incomplete defecation, and no subject "often" felt incomplete defecation. Only 12.5% of the subjects "sometimes" felt incomplete defecation. In other words, the administration of prebiotic composition reduced incomplete defecation, thereby facilitating defecation of the subjects.

Figure 11:
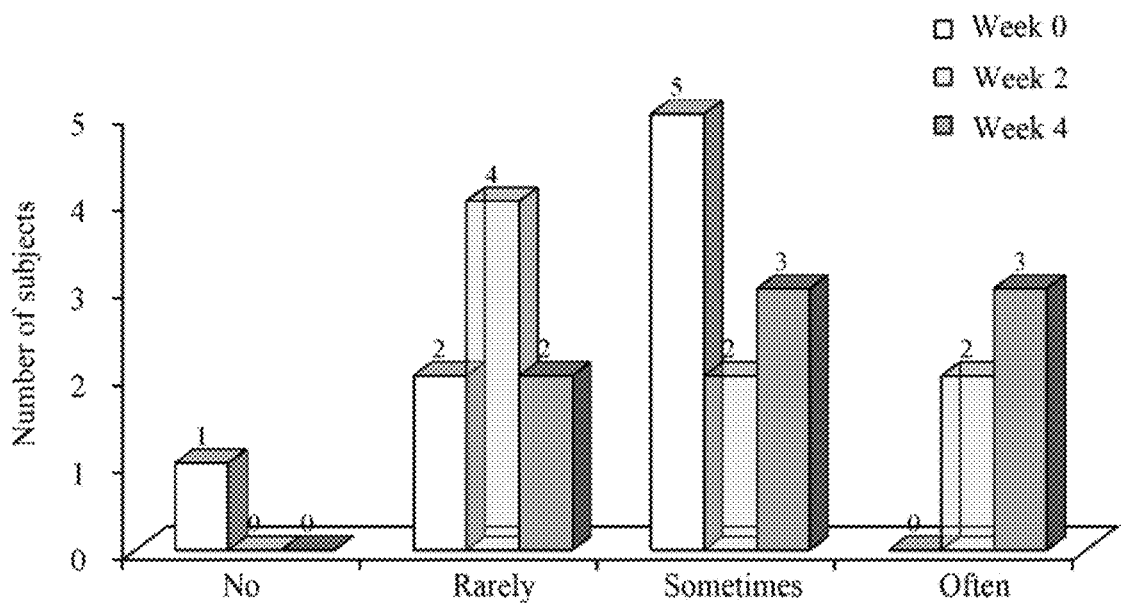
FIG. 11 is a graph showing an analysis result of a prebiotic composition on the intestinal peristalsis frequency of subjects.

Referring to FIG. 11, before taking the prebiotic composition at week 0, in the 8 subjects, no subject "often" felt intestinal peristalsis, 1 subject felt "no" intestinal peristalsis, 2 subjects "rarely" felt intestinal peristalsis, and 5 subjects "sometimes" felt intestinal peristalsis. After taking the prebiotic composition for 2 weeks, 2 subjects "often" felt intestinal peristalsis, no subject felt "no" intestinal peristalsis, and the quantity of subjects who "rarely" and "sometimes" felt intestinal peristalsis is 6. After taking the prebiotic composition for 4 weeks, 3 subjects "often" felt intestinal peristalsis, no subject felt "no" intestinal peristalsis, 3 subjects "sometimes" felt intestinal peristalsis, and 2 subjects "rarely" felt intestinal peristalsis. Therefore, the 8 subjects had an increased frequency of feeling intestinal peristalsis after taking the prebiotic composition for 4 weeks. Based on this, the administration of prebiotic composition promoted intestinal peristalsis, thereby improving the intestinal tract and promoting bowel movement, and thus facilitating defecation of the subjects.

Example 5-4. Analysis on Body Composition of Subject

The body composition of 8 subjects before taking the prebiotic composition (that is, at week 0) and after taking the prebiotic composition (that is, at week 2 and week 4) was measured by using a body fat meter (with a model of TANITA BC-601FS) and a tape measure. The body composition results of the 8 subjects were recorded as shown in FIG. 12 to FIG. 15.

Herein, the analyzed body composition items included: weight, whole body fat percentage, trunk fat percentage, and waist circumference.

Figure 12:
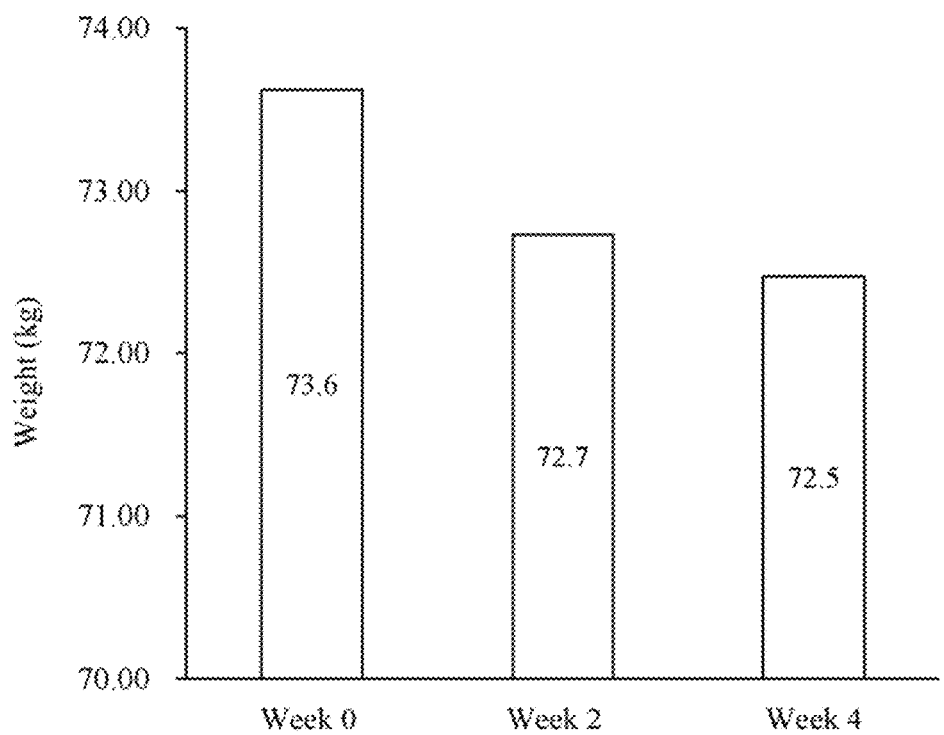
FIG. 12 is an analysis graph of an average weight of subjects at week 0, week 2, and week 4.

Referring to FIG. 12, before taking the prebiotic composition at week 0, the average weight of the 8 subjects was 73.6 kg, and after taking the prebiotic composition for 2 weeks, the average weight of the 8 subjects was reduced to 72.7 kg. After taking the prebiotic composition for 4 weeks, the average weight of the 8 subjects was further reduced to 72.5 kg. In other words, the subjects after taking the prebiotic composition for 2 weeks have an average weight reduced by 0.9 kg, and the subjects after taking the prebiotic composition for 4 weeks had an average weight reduced by 1.1 kg. Based on this, the administration of prebiotic composition composed of kiwifruit fermented product, inulin, and fructooligosaccharide effectively reduced the weight of subjects to achieve slimming.

Figure 13:
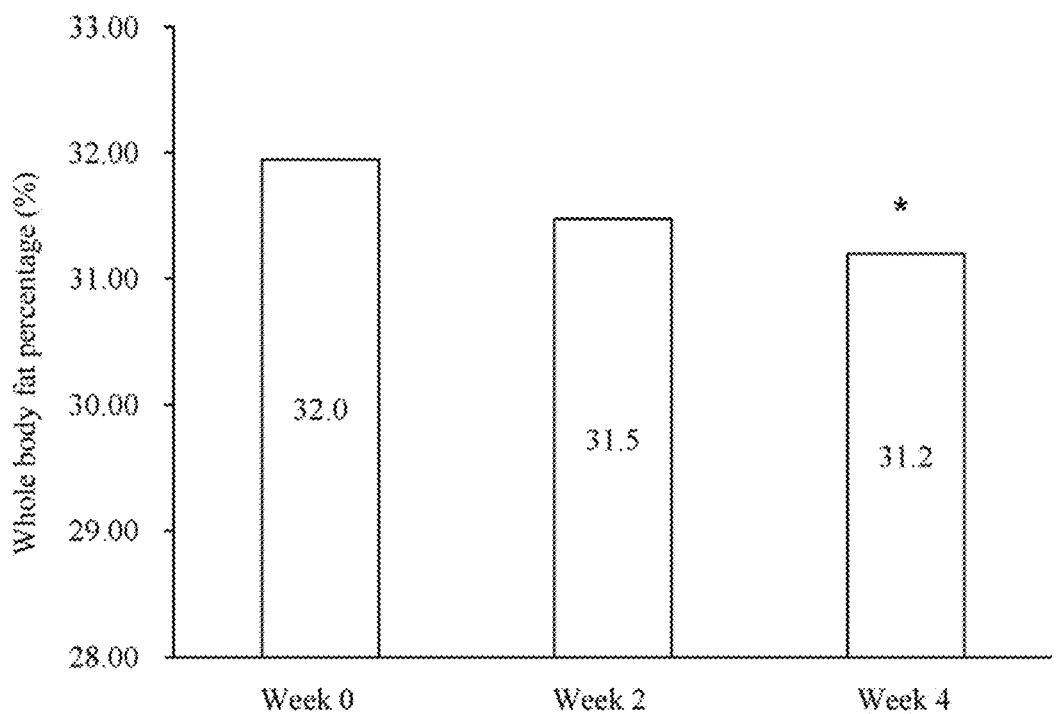
FIG. 13 is an analysis graph of an average whole body fat percentage of subjects at week 0, week 2, and week 4.

Referring to FIG. 13, before taking the prebiotic composition at week 0, the average whole body fat percentage of the 8 subjects was 32%, and after taking the prebiotic composition for 2 weeks, the average whole body fat percentage of the 8 subjects was reduced to 31.5%. After taking the prebiotic composition for 4 weeks, the average whole body fat percentage of the 8 subjects was further reduced to 31.2%. In other words, the subjects after taking the prebiotic composition for 2 weeks had an average whole body fat percentage reduced by 0.5%, and the subjects after taking the prebiotic composition for 4 weeks had an average whole body fat percentage reduced by 0.8%. Based on this, the administration of prebiotic composition composed of kiwifruit fermented product, inulin, and fructooligosaccharide effectively reduced the whole body fat percentage of subjects to achieve slimming.

Figure 14:
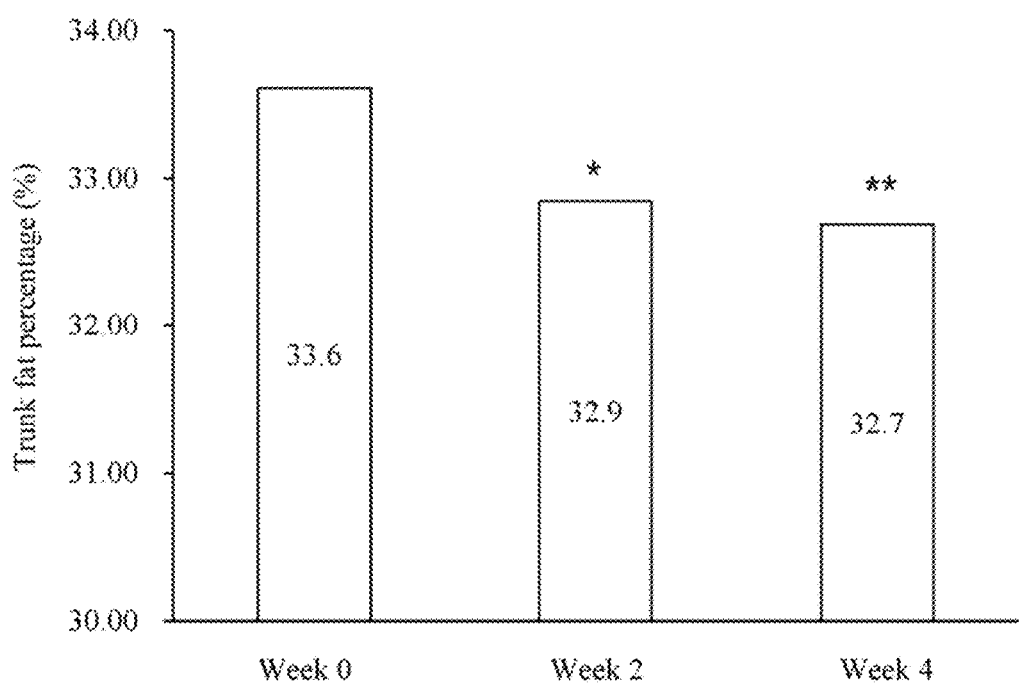
FIG. 14 is an analysis graph of an average trunk fat percentage of subjects at week 0, week 2, and week 4.

Referring to FIG. 14, before taking the prebiotic composition at week 0, the average trunk fat percentage of the 8 subjects was 33.6%, and after taking the prebiotic composition for 2 weeks, the average trunk fat percentage of the 8 subjects was reduced to 32.9%. After taking the prebiotic composition for 4 weeks, the average trunk fat percentage of the 8 subjects was further reduced to 32.7%. In other words, the subjects after taking the prebiotic composition for 2 weeks had an average trunk fat percentage reduced by 0.7%, and the subjects after taking the prebiotic composition for 4 weeks had an average trunk fat percentage reduced by 0.9%. Based on this, the administration of prebiotic composition composed of kiwifruit fermented product, inulin, and fructooligosaccharide effectively reduced the trunk fat percentage of subjects to achieve slimming.

Figure 15:
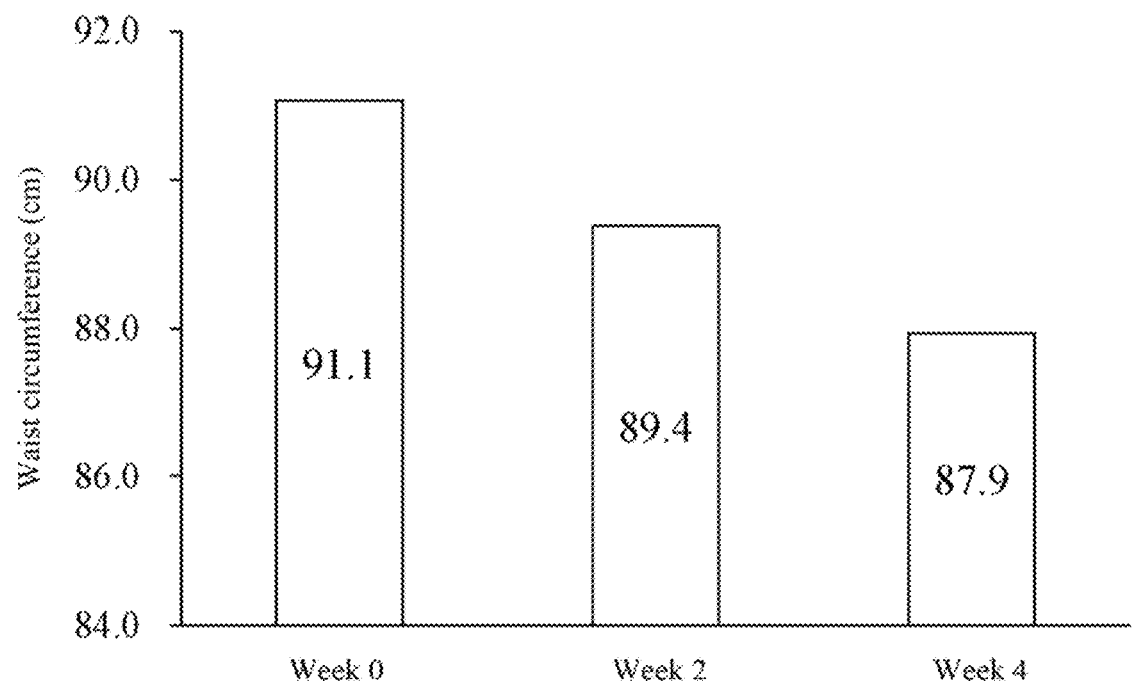
FIG. 15 is an analysis graph of an average waist circumference of subjects at week 0, week 2, and week 4.

Referring to FIG. 15, before taking the prebiotic composition at week 0, the average waist circumference of the 8 subjects was 91.9 cm, and after taking the prebiotic composition for 2 weeks, the average waist circumference of the 8 subjects was reduced to 89.4 cm. After taking the prebiotic composition for 4 weeks, the average waist circumference of the 8 subjects was further reduced to 87.9 cm. In other words, the subjects after taking the prebiotic composition for 2 weeks had an average waist circumference reduced by 1.7 cm, and the subjects after taking the prebiotic composition for 4 weeks had an average waist circumference reduced by 3.2 cm. Based on this, the administration of prebiotic composition composed of kiwifruit fermented product, inulin, and fructooligosaccharide effectively reduced the waist circumference of subjects to achieve slimming.

Figure 16:
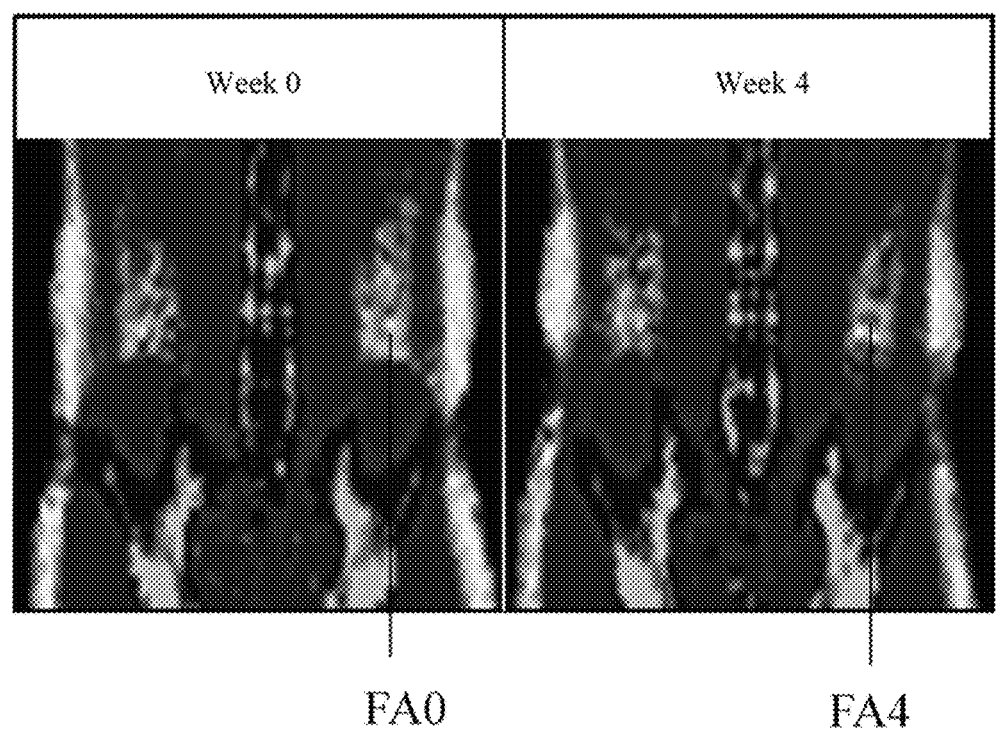
FIG. 16 is an analysis image of belly fat of a subject at week 0 and week 4.

In addition, as shown in FIG. 16, one of the eight subjects was detected on the change in belly fat at week 0 and week 4 by using a bone density and body composition analyzer (DXA). FA0 represents belly fat of the subject at week 0 (as shown in the white regions on both upper sides of the spine in the left panel in FIG. 16). FA4 represents belly fat of the subject at week 4 (as shown in the white regions on both upper sides of the spine in the right panel in FIG. 16). It can be found by comparing FA0 with FA4 that the belly fat of the subject is significantly reduced. In other words, the administration of prebiotic composition composed of kiwifruit fermented product, inulin, and fructooligosaccharide can effectively reduce the belly fat of subjects to achieve slimming.

In summary, the prebiotic composition including the kiwifruit fermented product, inulin, and fructooligosaccharide according to any embodiment of the present invention can be used for improving the intestinal tract of the subjects. The weight ratio of the kiwifruit fermented product, the inulin, and the fructooligosaccharide that are included in the prebiotic composition is 3-4:2.5-4:2.5-4. In some embodiments, the prebiotic composition including the kiwifruit fermented product, inulin, and fructooligosaccharide can be used for improving the intestinal flora (such as *Akkermansia muciniphila, Parabacteroides goldsteinii*, and *Bifidobacterium*), improving bowel movement of the subject (such as reducing the defecation difficulty of the subject, promoting the intestinal peristalsis frequency of the subject, reducing the incomplete defecation of the subject, reducing the defecation time of the subject, or a combination thereof), improving the intestinal barrier of the subject (such as increasing the concentration of tight junction protein in the subject), or a combination thereof. In addition, in some embodiments, the prebiotic composition including the kiwifruit fermented product, inulin, and fructooligosaccharide can be used for reducing the subject's weight, waist circumference, body fat percentage, or a combination thereof, so as to achieve weight loss.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for promoting growth of *Parabacteroides goldsteinii* in a subject in need thereof, comprising administering an effective dose of a prebiotic composition to the subject, wherein the prebiotic composition consisting of a kiwifruit fermented product, inulin, and fructooligosaccharide,
   wherein a weight ratio of the kiwifruit fermented product, the inulin, and the fructooligosaccharide is 3-4:2.5-4:2.5-4,
   wherein the kiwifruit is *Actinidia deliciosa*, and
   wherein the kiwifruit fermented product is obtained by the steps of: fermenting *Actinidia deliciosa* with 0.1% *Saccharomyces cerevisiae* for 1 day at 30° C. to obtain an initial fermentation broth, and fermenting the initial fermentation broth with 0.05% *Streptococcus thermophilus* for 1 day at 30° C. to obtain the kiwifruit fermented product.

2. The method according to claim 1, wherein the prebiotic composition improves bowel movement of the subject, intestinal barrier of the subject, or a combination thereof.

3. The method according to claim 2, wherein the improvement of bowel movement of the subject comprises reducing defecation difficulty of the subject, promoting intestinal peristalsis frequency of the subject, reducing incomplete defecation of the subject, reducing defecation time of the subject, or a combination thereof.

4. The method according to claim 2, wherein the prebiotic composition is used for increasing a concentration of a tight junction protein in the blood of the subject.

5. The method according to claim 4, wherein the tight junction protein is claudin 3 (CLDN3).

6. The method according to claim 1, wherein the prebiotic composition is used for reducing the subject's weight, waist circumference, body fat percentage, or a combination thereof.

7. The method according to claim 1, wherein the effective dose is 800 mg/day.

8. The method according to claim 1, wherein the weight ratio of the kiwifruit fermented product, the inulin, and the fructooligosaccharide is 4:3:3.

9. A method for increasing a concentration of a tight junction protein in blood of a subject in need thereof, comprising administering an effective dose of a prebiotic composition to the subject,
   wherein the prebiotic composition consisting of a kiwifruit fermented product, inulin, and fructooligosaccharide,
   wherein a weight ratio of the kiwifruit fermented product, the inulin, and the fructooligosaccharide is 3-4:2.5-4:2.5-4,
   wherein the kiwifruit is *Actinidia deliciosa*, and
   wherein the kiwifruit fermented product is obtained by the steps of: fermenting *Actinidia deliciosa* with 0.1% *Saccharomyces cerevisiae* for 1 day at 30° C. to obtain an initial fermentation broth, and fermenting the initial fermentation broth with 0.05% *Streptococcus thermophilus* for 1 day at 30° C. to obtain the kiwifruit fermented product,
   wherein the tight junction protein is claudin 3 (CLDN3).

* * * * *